United States Patent [19]

Iversen

[11] Patent Number: 5,618,796
[45] Date of Patent: Apr. 8, 1997

[54] METAL BINDING OLIGONUCLEOTIDE AND METHODS AND COMPOSITIONS FOR THEIR USE TO TREAT METAL TOXICITY

[75] Inventor: Patrick L. Iversen, Omaha, Nebr.

[73] Assignee: The Board of Regents of the University of Nebraska, Lincoln, Nebr.

[21] Appl. No.: 759,841

[22] Filed: Sep. 12, 1991

[51] Int. Cl.$^6$ .................. A01N 43/04; A61K 31/70; C07H 21/04; C12N 15/06
[52] U.S. Cl. .................. 514/44; 435/172.3; 536/23.1
[58] Field of Search .................. 514/44; 536/23.1; 435/172.3

[56] References Cited

U.S. PATENT DOCUMENTS

| | | | |
|---|---|---|---|
| 5,070,104 | 12/1991 | Pariza | 514/549 |
| 5,276,019 | 1/1994 | Cohen et al. | 514/44 |

FOREIGN PATENT DOCUMENTS

| | | |
|---|---|---|
| 0369458 | 5/1990 | European Pat. Off. . |
| 4040474 | 12/1990 | Germany . |

OTHER PUBLICATIONS

Westermann, "Inhibition of Expression of SV40 Virus Large T-Antigen by Antisense Oligodeoxyribonucleotides", *Biomed.Biochim.Acta* 48:1, 85–93 (1989).

James, "Towards Gene-Inhibition Therapy: A Review of Progress and Prospects in the Field of Antiviral Antisense Nucleic Acids and Ribozymes", *Antiviral Chemistry & Chemotherapy* (1991) 2(4), 191–214.

Marshall, "Phosphorodithioate DNA as a Potential Therapeutic Drug", *Science* (1993) vol. 259, pp. 1564–1570.

Agrawal, "Pharmacokinetics, Biodistribution, and Stability of Oligodeoxynucleotide Phosphorothioates in Mice", *Proc. Natl.Acad.Sci.USA*, (1991) vol. 88, 7595–7599.

Uhlmann, "Antisense Oligonucleotides: A New Therapeutic Principle", *Chemical Reviews* (1990) vol. 90, No. 4, 544–584.

M. Rothenberg et al., "Oligodeoxynucleotides as Anti-Sense Inhibitors of Gene Expression: Therapeutic Implications", Journal of the National Cancer InstituT, issued 18 Oct. (1989) *Commentary* vol. 81, No. 20:pp.1539–1544.

Biochemistry, vol. 23, issued 1984, V.L. Pecoraro et al., "Stability Constants of $Mg^{2+}$ and $CD^{2+}$ Complexes of Adenine Nucleotides and Thionucleotides and Rate Constants for Formation and Dissociation of MgATP and MgADP", pp. 5262–5271, especially p. 5264.

Journal of the National Cancer Institute, vol. 81, No. 20, issued Oct. 18, 1989, M. Rothenberg et al., "Oligodeoxynucleotides as Anti–Sense Inhibitors of Gene Expression: Therapeutic Implications", pp. 1539–1544, especially p. 1543.

Nature, vol. 299, issued Oct. 28, 1982, M. Karin et al., "Human Metallothionein Genes—Primary Structure of the Metallothionein–II Gene and a Related Processed Gene", pp. 797–802, especially p. 799.

Proceedings of the National Academy of Sciences, vol. 86, issued Jun. 1989, M. Matsukura et al., "Regulation of viral Expression of Human Immunodeficiency Virus in vitro by an Antisense Phosphorothioate Oligonucleotide Against *rev* (*art/trs*) in Chronically Infected Cells", pp. 4244–4248, especially p. 4245.

Toxicology, vol. 62, issued 1990, M. M. Jones et al., "The Search for Chelate Antagonists for Chronic Cadmium Intoxication", pp. 1–25, especially pp. 2, 6, 13, 19.

Marcus-Sekyra et al. 1987. Nucleic Acid Research 15(14): 5749–5763.

Kelley et al. 1988 Science 241: 1813–1815.

Iversen, 1991. Anti-cancer Drug Design 6:531–538.

*Primary Examiner*—Brian R. Stanton
*Attorney, Agent, or Firm*—Zarley, McKee, Thomte, Voorhees, & Sease

[57] ABSTRACT

The present invention discloses novel methods and compositions useful for removing toxic heavy metals from a host organism containing detectable levels of such heavy metals. The method comprises administering to the host organism a therapeutically effective amount of a heavy-metal binding agent which, when saturated with heavy metal atoms, is readily excreted from the body. In a preferred embodiment of the present invention, the binding agent is an oligomeric phosphorothioate oligonucleotide.

5 Claims, 1 Drawing Sheet

5,618,796

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 27 nucleotide bases
        ( B ) TYPE: nucleic acid
        ( C ) STRANDEDNESS: single
        ( D ) TOPOLOGY: linear ( i i ) MOLECULE TYPE: cDNA to a mRNA ( i i i ) HYPOTHETICAL: no ( i v ) ANTI-SENSE: yes ( x ) PUBLICATION INFORMATION:
        ( A ) AUTHORS: Matsukura, et al.
        ( B ) TITLE: Regulation of viral expression of human
            immunodeficiency virus in-vitro by an
            antisense phosphorothioate oligodeoxy-
            nucleotide against rev(art/tra) in
            chronically infected cells
        ( C ) JOURNAL: Proc. Natl. Acad. Sci. USA
        ( D ) VOLUME: 86
        ( E ) ISSUE: 06
        ( F ) PAGES: 4244
        ( G ) DATE: 1989

( x i ) SEQUENCE DESCRIPTION: SEQUENCE ID NO:1:

```
TCGTCGCTGT    CTCCGCTTCT    TCCTGCC                                           27
```

( 2 ) INFORMATION FOR SEQ ID NO:2:

( i ) SEQUENCE CHARACTERISTICS:
        ( A ) LENGTH: 18 nucleotide bases
        ( B ) TYPE: nucleic acid
        ( C ) STRANDEDNESS: single stranded
        ( D ) TOPOLOGY: linear ( i i ) MOLECULE TYPE: cDNA to a mRNA ( i i i ) HYPOTHETICAL: no ( i v ) ANTI-SENSE: yes ( v i i i ) POSITION IN GENOME:
        ( A ) CHROMOSOME/SEGMENT: 16q21- q22.1.
        ( B ) MAP POSITION: 844 through 861
        ( C ) UNITS:

( x ) PUBLICATION INFORMATION:
        ( A ) AUTHORS: Karin, M., and Richards, R. I.
        ( B ) TITLE: Human metallothionein genes-primary
            structure of the Metallothionein-II gene and
            a related processed gene
        ( C ) JOURNAL: Nature
        ( D ) VOLUME: 299
        ( E ) ISSUE: 43
        ( F ) PAGES: 797
        ( G ) DATE: 1982

( x i ) SEQUENCE DESCRIPTION: SEQUENCE ID NO:2:

```
GGCGCAGGAG CAGTTGGG                                                                          18
```

( 2 ) INFORMATION FOR SEQ ID NO:3:

( i ) SEQUENCE CHARACTERISTICS:
        ( A ) LENGTH: 18 nucleotide bases
        ( B ) TYPE: nucleic acid
        ( C ) STRANDEDNESS: single
        ( D ) TOPOLOGY: linear ( i i ) MOLECULE TYPE: cDNA to a mRNA ( i i i ) HYPOTHETICAL: no ( i v ) ANTI-SENSE: yes ( v i i i ) POSITION IN GENOME:
        ( A ) CHROMOSOME/SEGMENT: 16q21- q22.1.
        ( B ) MAP POSITION: 844 through 861
        ( C ) UNITS:

( x ) PUBLICATION INFORMATION:
        ( A ) AUTHORS: Karin, M., and Richards, R. I.
        ( B ) TITLE: Human metallothioncin genes-primary
            structure of the Metallothioncin-II gene and
            a related processed gene
        ( C ) JOURNAL: Nature
        ( D ) VOLUME: 299
        ( E ) ISSUE: 43
        ( F ) PAGES: 797
        ( G ) DATE: 1982

( x i ) SEQUENCE DESCRIPTION: SEQUENCE ID NO:3:

```
CCCAACTGCT CCTGCGCC                                                                          18
```

METAL BINDING OLIGONUCLEOTIDE AND METHODS AND COMPOSITIONS FOR THEIR USE TO TREAT METAL TOXICITY

FIELD OF THE INVENTION

The present invention relates to methods and compositions useful in removing metal atoms, and, in particular toxic heavy metal atoms, from a host organism which contains undesirable levels of such metals. In a preferred embodiment, the present invention includes the use of phosphorothioate oligodeoxyribonucleotides ("PS-ODNs") in such methods. An especially preferred embodiment, encompasses removing toxic metals from a host by use of an antisense phosphorothioate oligonucleotide which also inhibits the in vivo synthesis of metallothioneins which, as explained hereinafter, interfere with the effective removal of toxic metals.

BACKGROUND AND OBJECTIVES OF THE INVENTION

In the following discussion, a number of citations from professional journals are included for the convenience of the reader. While these citations more fully describe the state of the art to which the present invention pertains, the inclusion of these citations is not intended to be an admission that any of the cited publications represent prior art with respect to the present invention.

The ingestion of toxic metals is an extremely serious health problem in the United States, as well as in many other industrialized nations of the world. Poisoning with cadmium, lead and/or mercury, for example, is surprisingly common, affecting about 1 in every 200 persons in this country. This level of public poisoning is unusually high, given society's awareness of the toxicity of these metals.

In general, the metals considered to be toxic to host organisms are the nutritionally-nonessential heavy metals such as cadmium, lead, cesium, arsenic and mercury. These metal elements are toxic when ingested in any amount, and regardless of the route of entry. Their toxicity derives from their capacity to successfully compete with nutritionally-essential metal elements in metabolic pathways, and to form stable coordination complexes with a variety of binding agents (or "ligands") in these pathways. Because there are no known metabolic requirements for these heavy metal elements in animal nutrition, their ingestion is usually associated with undesirable (sometimes severe) side effects. However, as discussed more fully hereinafter, certain other metals which are relatively nontoxic and are, in fact, essential trace mineral elements needed in nutrition, such as, for example, calcium, magnesium, iron, zinc, and copper can, under certain conditions, also be deleterious to the host and the resulting toxicity can be treated using the methods and compounds of this invention.

The serious problem of metal poisoning occurs most frequently in 1) children (commonly from economically deprived families) who are exposed to these toxic metals in contaminated soil, air and dust of the home environment; and in 2) workers in industry who are contaminated by the heavy metals used as reagents in their workplace. Unfortunately, almost all of the toxic heavy metal atoms ingested or adsorbed remain bound in the tissues of these individuals, where they continue to do damage by competing with essential metal elements in metabolic pathways, interfering (often significantly) with the normal development and functioning of the contaminated individual.

The standard therapeutic procedures used today for treating heavy metal poisoning in individuals are slow, often painful, and use chemical reagents which are themselves sometimes very toxic, damaging the kidneys in the process of capturing the heavy metal atoms and transporting them to the bladder for excretion. Examples of such heavy metal binding agents being used in therapy are diethyldithiocarbamate (Berry et al., *J. Clin. Oncol.* 8: 1585, 1990; also, see review by G. Renoux, *J. Pharmacol.* 13 (suppl. 1): 95, 1982); 2,3-dimercapto-1-propanol ("Dimercaprol") (U.S. Pat. No. 2,402,665); and N-acetylcysteine (Hjortso et al., *Eur. J. Clin. Pharmacol.* 39: 29, 1990). This lack of effective, convenient and nontoxic therapeutic agents for treating metal poisoning is a major problem in society. It is one object of this invention to provide a new class of binding agents which are safe and effective and overcome these general problems of the prior art compounds.

However, for a therapeutic agent to be truly effective in treating metal poisoning, it should not only have the capacity to bind metal atoms, but also to inhibit the synthesis of metallothioneins ("MTs"). Toxic metal atoms remain in tissues because the body traps the toxic metals in the tissues with metallothioneins. These are low molecular weight, cysteine-rich proteins with a high affinity for metal atoms (e.g., see the review by D. H. Hamer, *Annu. Rev. Biochem.* 55: 913, 1986; GK Andrews, *Prog. Food Nutr. Sci.* 14: 193, 1990). With a half-life of just a few days, the metallothioneins effectively bind metal atoms, sequestering them in the tissues of the body, then passing the metal atoms on to newly synthesized metallothioneins as they themselves begin to degrade. The problem with this physiologic response is that the metallothioneins are only effective at defensively sequestering the metal atoms; they are completely ineffective at removing them from the body of the host. Thus, this metallothionein response by the body does not abrogate the toxic metal problem. For example, the half-life for cadmium in the human body is estimated to be about 30 years (Jones & Cherian, *Toxicology* 62: 1, 1990); that for lead is considered to be even longer.

Thus, another object of this invention is to provide a class of binding agents which have the capacity not only to bind metal atoms, but also to inhibit the synthesis of new metallothioneins, so that the metal atoms released by the breakdown of old metallothioneins will be captured by the therapeutic agent and removed from the body. To date no effective therapeutic agents are believed to exist which can be used for these dual purposes.

Accordingly, it is a principal object of the present invention to provide a safe and effective method for binding and removing metals from host organisms.

It is another object of the present invention to provide compounds which are effective metal-binding agents which can be employed therapeutically to bind and remove even toxic heavy metals by excretion from a host organism.

It is yet another object of the present invention to use antisense PS-ODNs as sequence-specific inhibitors of metallothionein protein synthesis while they simultaneously bind available metal ions in the tissues being treated.

It is still another object of the present invention to provide pharmaceutical compositions comprising therapeutically effective amounts of a metal binding agent, together with pharmaceutically-acceptable excipients and carriers, in forms capable of chelating metal atoms and being excreted from the body.

SUMMARY OF THE INVENTION

In accordance with this invention, there is provided a novel method for removing toxic metals from a host organism containing undesirable levels of such metals. The method comprises administering to the host organism a therapeutically effective amount of a novel metal binding agent which, when it binds metal ions, is readily excreted from the body. The novel binding agent can be an oligomeric phosphorothioester compound, for example having the following formula:

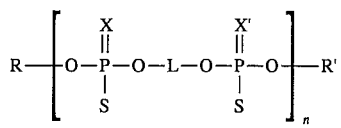

wherein "L" is a linking group, X and X' are the same or different and are oxygen or sulfur, R and R' can be the same or different and are unsubstituted or substituted moieties at the termini of the molecule, and "n" is the number of repeat units, and in general can be between about 2 to and about 30 and even greater. Exemplary of L, R, and R' are, for example, a deoxyribonucleotide moiety or a ribonucleotide moiety (including the glycosidic alpha- and beta- congeners), a deoxyribose moiety, or a ribose moiety. In addition, R and R' can be hydrogen, a reporter group, such as a fluorophore (defined more fully hereinafter), or a ligand which, in many cases is a substituent which is specific for the organ targeted for metal removal. In general, for the oligomeric compounds of this invention to be useful as a metal binding agent in the present invention, the linking group L and the terminal groups R and R' must not interfere in the capacity of the sulfur ligands to chelate the toxic heavy metal atoms, and must permit the molecule to be readily transported both into and out of the cells and tissues which harbor the targeted metals.

In an especially preferred embodiment of the present invention, the linking group L, and the terminal groups R and R', are deoxyribonucleotide moieties, and the metal binding agent is a phosphorothioate oligodeoxyribonucleotide (PS-ODN) molecule such as described in Zon et al., European Patent Application #88302617.1, the disclosure of which is incorporated herein by reference. The following formula is exemplary:

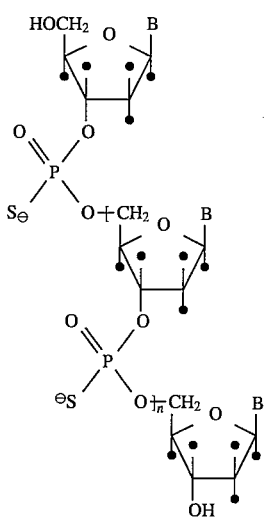

where "B" is a deoxyribonucleotide base selected from the group consisting of adenosine, guanosine, cytosine, and/or thymidine, and the number of repeating units "n" is between about 2 and about 30.

The particular sequence of nucleotide bases in the PS-ODN is dependant on many factors. For example, when the PS-ODN is an antisense molecule, the nucleotide base sequence must be complementary, or at least substantially complementary, to that of a known gene or messenger RNA (mRNA) molecule in the host. On the other hand, when binding to host genes or mRNAs is to be avoided, then the nucleotide base sequence in the PS-ODN will have a non-physiologic sequence, such as is found in a poly-G, a poly-C, or a poly-GC sequence.

Instruments for the automated synthesis of PS-ODNs are available commercially. Exemplary is the Model 380B DNA synthesizer, manufactured by Applied Biosystems, Inc. (ABI, Foster City, Calif.). Synthesis of PS-ODNs using such instruments is routine and is well known to those skilled in the art.

Where the linking group L is a ribonucleotide moiety, the metal binding agent is a phosphorothioate oligoribonucleotide molecule. Such a molecule would have the following general formula, in which "B" is a ribonucleotide base selected from the group consisting of adenine, guanine, cytosine, and uridine, and the number of repeating units "n" is from 2 to 30:

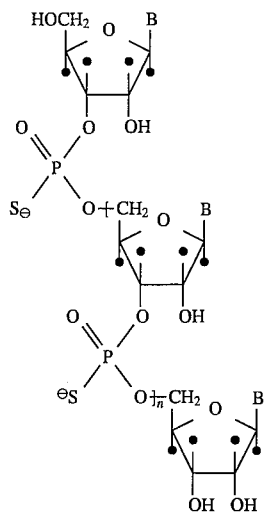

Where L is either a deoxyribose moiety or a ribose moiety, the oligomeric phosphorothioester has no nucleotide bases along its phosphorothioate backbone. It may be desirable that the terminal groups R and R' be deoxyribonucleotides or ribonucleotides in order to facilitate cellular transport. In carrying out this invention, any oligomeric structure can be used as a metal binding agent, provided it has the capacity to be readily transported both into and out of cells which harbor the targeted metals.

Antisense oligodeoxyribonucleotides. In a preferred embodiment of the present invention, a PS-ODN is used which has the dual function of i) binding heavy metal ions to its phosphorothioate backbone, and ii) blocking the synthesis of heavy metal-binding metallothioneins. This latter function is accomplished when the PS-ODN has a nucleotide base sequence which is antisense to a critical portion of a gene responsible for production of the metal-binding metallothionein proteins. By blocking production of metallothionein, the PS-ODN reduces, and in some cases eliminates, the undesirable long-term sequestering of toxic heavy metals by metallothionein into various tissues of the body. This leaves more of the toxic metal ions free in solution and available for binding and subsequent removal by the PS-ODN.

The compounds of the present invention have been found to bind heavy metals when used at low concentrations of approximately 1–20 micromolar in vitro. In vivo, it is preferred to attain a concentration of the active ingredient of from about 0.1 micromolar to about 100 micromolar in blood. This in vivo concentration can be achieved in a variety of dosage methods described hereinafter.

In practicing the methods of the present invention, the concept of a "therapeutically effective amount" is that amount of metal binding agent which is a) sufficient both to bind the detectable toxic heavy metal ions and to abrogate their toxic effects; b) well tolerated by the host organism; and c) does not cause any undesirable side effects. As a general rule, the appropriate therapeutic doses are not large, and would be no greater than that which can be absorbed by the host organism. In using the term "detectable," it is assumed that the methods utilized to detect the heavy metal ions are the usual and common methods available to a person skilled in the art of such detection.

It is to be understood that the metal binding agents of the present invention can be utilized in a wide variety of host organisms, mammals and, in particular humans, being the most commonly treated in accordance with this invention. It should be understood, however, that the methods and compositions of the present invention can be used to remove metals from virtually any host.

DETAILED DESCRIPTION OF THE INVENTION

Metals

Figure 1:
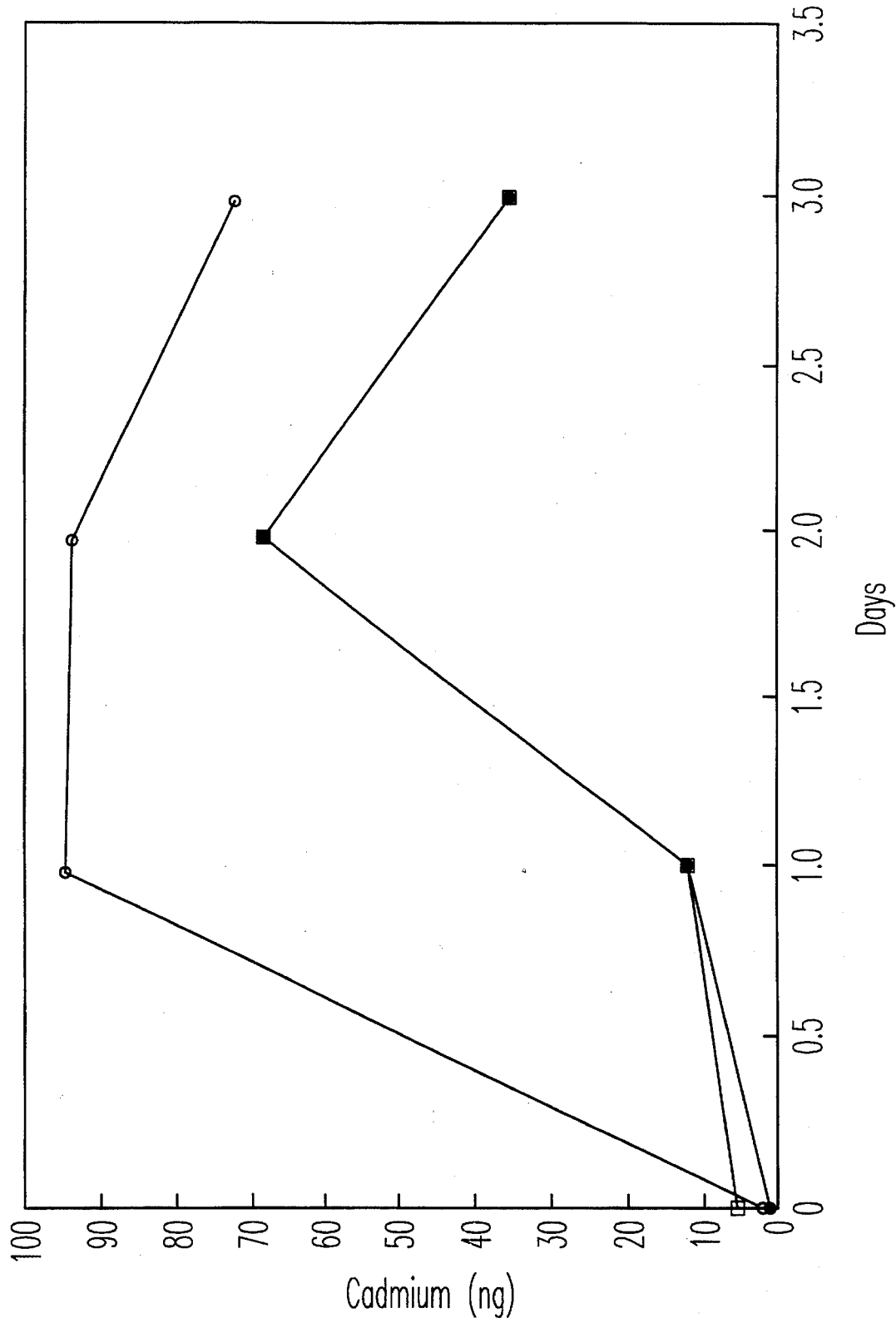
FIG. 1 is a line graph demonstrating average cadmium levels (in nanograms) in each of three 24-hour volumes of urine from animals which had received therapeutic phosphorothioate oligodeoxyribonucleotide (PS-ODN) only, cadmium only, or a combination of PS-ODN and cadmium.

Generally, any metal which binds to a phosphorothioate moiety is a target metal for the methods of this invention. As a practical matter, the metal targeted for removal is generally one which is toxic to the host. Exemplary of these toxic metals are the heavy metals lead, mercury, cadmium, strontium, uranium, arsenic and cesium. In contrast, certain other metals are relatively nontoxic and are, in fact, essential trace mineral elements needed in nutrition, such as, for example, calcium, magnesium, iron, zinc, and copper. It is believed that the novel binding agents of this invention will not deleteriously alter the levels of essential trace metal elements. As shown below in TABLE 1 of the present disclosure, PS-ODNs do not bind essential trace metal elements as readily as they do toxic heavy metal atoms. Recent evidence indicates that these essential elements, when present in trace amounts, are not readily bound by the chelating agents used to capture and remove toxic heavy metal elements. For example, when the heavy-metal chelating agent N-acetylcysteine was administered intravenously in high doses for 2 weeks to healthy volunteers, it did not reduce detectable concentrations of essential trace metal elements in the blood (E. Hjortso et al., *Eur. J. Clin. Pharmacol.* 39: 29, 1990). Therefore, this compositions and methods of this invention are particularly useful to treat heavy metal poisoning.

It should be noted, however, that to certain individuals even essential trace minerals can be toxic. For example, iron is toxic to people with hemochromatosis, an inherited disorder of metabolism that causes serious iron overload in the body. It is the most common genetic disease among caucasians, but is often not diagnosed by physicians. Although the number of victims is relatively small, they are subject to agonizing pain, irreversible damage to body organs, and an early death. While there is no cure for hemochromatosis, the only present therapy for this disease is monthly phlebotomy, or bloodletting. Clearly, this invention provides a better method for removing excess iron from individuals afflicted with this disorder.

Oligonucleotides

The size of the oligonucleotides of this invention, i.e., the number of bases in the oligonucleotide sequence, can vary over a wide range. Generally, the length (in base numbers) of a therapeutic oligonucleotide of the present invention ranges from at least about 4 bases to as many as about 50 bases. In practice the range is between about 4 and about 32 bases, i.e., between about 2 and about 30 repeating units (see the formula at page 7 herein. However, it is to be noted that the longer oligonucleotides can be more difficult and more costly to prepare and more difficult to handle, as well as being less efficient at penetrating the target tissue.

The nucleotide base sequence of the oligonucleotides of this invention can either be sequence non-specific or they can be complementary to the "sense" (information bearing) strand of the genes encoding the synthesis of metallothioneins. Such "antisense" oligonucleotides have become widely recognized in recent years for their ability to inhibit the expression of specific genes (Cohen J. S. [editor], *Oligodeoxyribonucleotides: Antisense Inhibitors Of Gene Expression*, CRC Press, Boca Raton, Fla., 1989). "Antisense" oligonucleotides are single-stranded nucleic acids which, by hybridizing either to the complementary DNA nucleotide sequence in a target gene, or, more commonly, to the messenger RNA (MRNA) transcribed from that gene, are able to completely abrogate the function of the targeted gene. Because antisense oligonucleotides target RNA or DNA rather than proteins, they are drugs that can be orders of magnitude more selective than traditional drugs, a factor which should very significantly reduce problems of unwanted side effects.

Therefore, according to the present invention, PS-ODNs are synthesized with a nucleotide sequence which is complementary to the gene message encoding the synthesis of metallothioneins; such antisense PS-ODNs have the capacity to block the synthesis of metal-sequestering metallothioneins while simultaneously binding heavy metal ions found in the tissues in an excretable form.

Design of PS-ODNs antisense to metallothioneins is possible because numerous metallothionein genes have been cloned and sequenced. In humans, two major forms of metallothionein (MT), MT-I and MT-II, have been identified and characterized. Five functionally-distinct MT-I genes and one functional MT-II gene have been characterized to date (Foster & Gedamu, *J. Biol. Chem.* 266: 9866, 1991), and their gene sequences are known. Regulation of synthesis of these proteins is at the level of transcription. Therefore, blocking the synthesis of metallothioneins by using antisense PS-ODNs at the level of MT-gene transcription reduces the concentration of metallothioneins in the various tissues of a host organism, thereby reducing the long-term sequestration in those tissues of metallothioneins saturated with heavy metal atoms.

Pharmaceutical Formulations Useful as Therapeutic Administration

In another embodiment of the present invention, pharmaceutical formulations are provided for use in therapy of individuals with detectable levels of heavy metal poisoning.

To be available for use in injection, oral or systemic administration for therapeutics, preparations of heavy metal binding agents must be formulated into suitable pharmaceutical compositions; the protocol for administration by a particular route would use a therapeutic approach compatible with the particular formulation selected. Pharmaceutical compositions within the scope of the present invention include those compositions where the metal binding agents are provided in an effective amount sufficient to bind all detectable non-essential heavy metals without causing unacceptable toxicity for the patient. The amount which represents a therapeutically-effective dose sufficient for treatment of host organisms such as, for example, a human individual, remains to be determined empirically by those skilled in the art of designing and administering immuno- and chemotherapy.

The heavy-metal binding agents of the present invention (also referred to hereinafter as the "active ingredients" or "active compounds"), in whatever analog prepared, may be administered in a pharmaceutical composition which contains, in addition to the active ingredient, any of a number of pharmaceutically-acceptable excipients which facilitate processing of the active compound into suitable pharmaceutical preparations. In a preferred embodiment, the preparations are designed for injection, similar to other therapeutic injectables already widely used. In another form, the therapeutic preparations may be administered by parenteral administration. Pharmaceutical compositions designed for oral administration in such forms as tablets, capsules, and dragees, or for rectal administration in the form of suppositories, are also considered to fall within the scope of the present invention.

Appropriate formulations of the therapeutic preparation for oral or parenteral administration include aqueous solutions of the active compound prepared in a water-soluble or water-dispersible form. As an injectable therapeutic, the active compounds may be administered as suspensions in appropriate oily injection carriers, i.e., in suitable lipophilic carriers, such as fatty oils (sesame oil being an example), or synthetic fatty acid esters (ethyl oleate or triglycerides being examples). Pharmaceutical formulations prepared for aqueous injection may contain substances which increase the viscosity of the suspension such as, for example, sodium carboxymethyl cellulose, sorbitol, and/or dextran.

The therapeutic compositions of the present invention may also be administered encapsulated in liposomes. In such pharmaceutical preparations, the active ingredients are contained in corpuscles which consist of concentric aqueous layers interspersed between hydrophobic lipidic layers. The compositions which contain the metal binding active ingredients, depending upon their solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, more or less ionic surfactants such as a diacetylphosphate, stearylamine, or phosphatidic acid, and/or other materials of a hydrophobic nature which are generally well known in the art.

Fluorophores

A wide range of fluorophores are known and used by those skilled in the art, including such compounds as, for example, fluorescein, rhodamine, tetramethyl rhodamine, sulpho-rhodamine 101, Texas Red, dansyl, and phycoerythrin, among others, and the biologically-acceptable salts thereof. In a preferred embodiment of the present invention, fluorescein isothiocyanate (FITC) is the fluorophore used to label the oligonucleotide probe.

U.S. Pat. No. 3,998,943 describes the preparation of a fluorescently labeled insulin derivative using fluorescein isothiocyanate (FITC) as the fluorescent label, and a fluorescently-labeled morphine derivative using 4-aminofluorescein hydrochloride as the fluorescent label. U.S. Pat. No. 4,420,568 to Wang et al., is directed to the use of triazinylamino-fluorescein moieties as fluorophores in fluorescence polarization techniques. Carboxyfluorescein has also been used for analytical determinations. R. C. Chen, *Analyt. Lett.* 10: 787 (1977) describes the use of carboxyfluorescein to indicate the activity of phospholipase. U.S. Pat. No. 4,476,229 to Fino et al., describes a series of amino acid amido derivatives of carboxyfluorescein useful as reagents in fluorescence polarization immunoassays. The selection of a particular fluorescent tracer for use is a matter of choice, given the teachings hereof, and is not crucial to the practice of the present invention.

Such fluorophores may be conveniently conjugated, for example, to an amino group of a polynucleotide by the use of, for example, isothiocyanate derivatives, succinimidyl esters or sulphonyl halide derivatives; or, fluorophores may be conjugated to thiol derivatized polynucleotides using, for example, maleimido derivatives. Other reactive derivatives of fluorophores are also known in the art, as shown, for example, in the catalogue of Molecular Probes, Inc.

The following examples more fully demonstrate this invention.

EXAMPLE 1

In vivo Use of a PS-ODN to Clear Cadmium from a Rodent Host

Animals. Male Sprague-Dawley rats (SASCO, Omaha, Neb.) with weights ranging from 150–180 grams were housed individually in separate metabolism cages. Rats were allowed free access to Purina Rodent Lab Chow 5001 standard powdered diet and tap water ad libitum.

PS-ODN synthesis. The PS-ODN chain-extension synthesis was performed on a 1-mole scale by use of an Applied Biosystems Model 380B DNA synthesizer and the recommended cycle for hydrogen phosphonate chemistry (Stec et al., *J. Amer. Chem. Soc.* 106: 6077, 1984). The PS-ODNs were purified by adsorption to and elution from Applied Biosystems "OPC" columns as described by the manufacturer in its product literature. The protocol was modified, however, by increasing the $CH_3CN$ concentration from 20 to 35% in the final elution step following the detritylation in situ with dilute trifluoroacetic acid. The eluant was then dried in a Savant DNA SpeedVac (SAVANT Instruments, Inc., Farmingdale, N.Y.) and stored at 4° C. until use.

For this study, a synthetic PS-ODN which was 27 nucleotide bases in length (a "27-mer") was selected for testing as a metal-binding agent. It was obtained from Applied Biosystems, Inc., where it was synthesized using the methods described in the previous paragraph. The particular PS-ODN obtained was identified as "MM3S-27" and has a nucleotide base sequence which blocks expression of the human immunodeficiency virus in chronically infected host cells. As far as is known, there is no equivalent nucleotide base sequence in the genome of the rat. The nucleotide base sequence of the MM3S-27 PS-ODN (as recorded by Matsukura et al., *Proc. Natl. Acad, Sci. U.S.A.* 86: 4244, 1989), is as follows:

SEQUENCE ID NO:1: 5'-TCGTCGCTGT CTCCGCTTCT TCCT-GCC-3'

Dose and route of administration. The PS-ODN was dissolved at a final concentration of 3 mg/ml in a sterile phosphate-buffered isotonic saline solution, pH 7.4. A bolus 0.3-mg dose was administered separately to each of four animals in a 100-microliter volume with a 1.0-cc syringe, via an intraperitoneal route. Four hours later, the host animal was given a single subcutaneous (intrascapular) of the heavy metal cadmium, injected at a concentration of 2.7 mg/kg body weight, and supplied as cadmium chloride ($CdCl_2$) dissolved in 0.1 ml normal saline (0.9% NaCl).

Specimen collection and processing. The urine from four animals was separately collected and stored. The 24-hour volumes of urine excreted by each animal were quantitated daily for three days following injection. The amount of cadmium excreted in the urine samples was determined by atomic absorption spectroscopy using an air-acetylene flame, and the average amount of cadmium (in nanograms) for all animals with the same treatment was plotted.

Results. The data from 3 animals were averaged and are shown in FIG. 1, which is a line graph demonstrating average cadmium levels (in nanograms) in each of three 24-hour volumes of urine from animals which had received either MM3S-27 PS-ODN only (closed squares), cadmium only (closed triangles), or a combination of PS-ODN and cadmium (closed diamond). While the amount of cadmium detected in urines peaked on day 2 in animals which received cadmium only, the total amount of cadmium detected (area under the curve) was small relative to the amount of cadmium which had been administered to the animal. In stark contrast, the amount of cadmium detected in the urines of animals which had received both cadmium and PS-ODN was substantially higher than cadmium-only animals on day 1, and remained so for the duration of the study (FIG. 1). The total amount of cadmium detected (area under the curve) in this latter group of animals was nearly all of the cadmium which had been administered to the animals.

EXAMPLE 2

Use of PS-ODN to Rescue a Host Animal Bearing Toxic Levels of Cadmium

A total of 8 rats were used in the studies herein reported. Experimental procedures and doses were as described in detail in the previous example, except as modified below. Of the 8 animals, 2 received cadmium only (as $CdCl_2$, 2.7 mg/kg body weight); 3 received SEQ ID NO:1, the MM3S-27 PS-ODN, only (1 milligram per animal); and 3 received a combination of both. In the latter, cadmium was administered subcutaneously (intrascapular) in a 100-microliter volume; the therapeutic PS-ODN was then administered 2 hours later, as a 100-microliter intraperitoneal injection, and every other day for 6 days. Four days after the final PS-ODN injection (on day 10), the animals were sacrificed and their tissues examined.

Cadmium excretion rose rapidly in the urines of animals treated with the PS-ODN after receiving the heavy metal, and absolutely no overt signs of cadmium toxicity (such as, for example., lethargy, ruffling of fur, loss of weight, kidney damage, immobility) appeared in these animals. Cadmium levels in blood and tissues dropped to non-detectable levels (as determined by atomic absorption spectroscopy) following therapy with PS-ODN, compared to control animals which received cadmium only. Virtually all the administered cadmium was excreted complexed to the PS-ODNs. No toxicity due to PS-ODNs were detected in any of the test animals or in the PS-ODN-only control animals.

In the cadmium-only control animals, metal toxicity was evident after two days, and was severe by the end of 10 days. Very little cadmium was detected in the urine of these toxemic rats; virtually all of the administered cadmium remained sequestered in their tissues.

These data demonstrate the unexpected utility and therapeutic efficacy of PS-ODN at binding toxic heavy metal atoms in an excretable form in animals exposed to toxic levels of heavy metals.

In the previous examples, the therapeutic PS-ODNs used had no known binding specificity for genes encoding any protein in the rat, including the metal-binding metallothioneins. In the following prophetic example, which demonstrates a preferred embodiment of the present invention where the host organism is a human, the therapeutic PS-ODNs are those which are specifically antisense to genes encoding human metallothioneins.

EXAMPLE 3

Use in humans of a PS-ODN Heavy Metal Binding Agent Which is also Antisense to Metallothionein Experimental procedures for preparation of therapeutic PS-ODNs are as described in the previous examples, except that the nucleotide base sequence of the PS-ODN used as the novel therapeutic metal-binding agent of the present invention is designed to be antisense to a metallothionein gene. Host individuals are placed in four different treatment groups, as follows:

1) individuals who have a known prior exposure to toxic heavy metals and who have detectable levels of toxic heavy metal ions, to receive PS-ODNs which are specifically antisense to a gene sequence for metallothionein;

2) individuals who have a known prior exposure to toxic heavy metals and who have detectable levels of toxic heavy metal ions, to receive PS-ODNs which are not antisense to metallothionein. The preferred PS-ODN administered to this control group of individuals is the PS-ODN which contains the "sense" sequence to the metallothionein gene used for group 1 above;

3) healthy volunteers who receive equivalent amounts of the antisense PS-ODN only; and 4) healthy volunteers who receive equivalent amounts of the sense PS-ODN only.

Oligonucleotides. Two complementary PS-ODNs are synthesized and tested, each of which are 18 nucleotide bases in length and associated with bases 7 to 24 downstream from the "ATG" translational start site of human metallothionein-II MRNA. The anti-MT antisense 18-mer sequence is as follows:

SEQUENCE ID NO:2: 5'-GGCGCAGGAG CAGTTGGG-3' and the complementary sense 18-mer sequence is as follows:

SEQUENCE ID NO:3: 5'-CCCAACTGCT CCTGCGCC-3'.

Therapeutic administration of PS-ODNs. In a preferred embodiment of the present invention, the oligonucleotide preparation is administered systemically via an intravenous route to individuals with heavy-metal poisoning. The PS-ODN is administered in an amount sufficient to bind the toxic metal atoms present in the individual. The effective amount of PS-ODN is that amount which is a) sufficient to bind the toxic metal atoms without causing unacceptable toxicity for the patient, and b) sufficient to block the synthesis of new metallothioneins as the tissue metallothioneins are degraded. This amount remains to be determined empirically by those skilled in the art of designing and administering chemotherapy. However, a preferred dosage comprises that which is sufficient to achieve an effective blood concentration of from about 0.1 to about 200 micromolar.

When a dose sufficient to demonstrate metal binding has been confirmed by detection of substantially increased levels of heavy metal atoms being excreted in the urine of the treated individual, additional antisense PS-ODNs are administered systemically to the patient in a low dose maintenance schedule, for the purpose of capturing and eliminating any remaining heavy metal atoms which are released from metallothioneins sequestered in the tissues of the patient prior to initiation of PS-ODN therapy. The pharmaceutical preparation used in this maintenance therapy contains one or more antisense oligonucleotides described as useful in the present invention.

When the clinical and toxicological data obtained during the treatment of the aforementioned groups are analyzed and compared, the therapeutic efficacy of anti-MT antisense PS-ODNs and control, "sense" PS-ODNs is then determined.

In the previous examples, the binding of heavy metals to PS-ODNs were carried out in vivo. Straightforward determination of binding affinities of a substantial number of different toxic heavy metals to these PS-ODNs was not practical. Accordingly, in the following example, the binding affinities of a PS-ODN for a variety of metal ion types was determined in vitro, so that straightforward comparisons can be made.

EXAMPLE 4

Heavy Metal Binding to a PS-ODN

To determine the in vitro heavy metal-binding capacity of PS-ODNs, SEQ ID NO:1, the MM3S-27 synthetic PS-ODN, was selected for testing. In this study, the PS-ODN was mixed with two different concentrations of heavy metal salts at ambient (room) temperature and centrifuged at approximately 10,000×g for 30 seconds to facilitate the association of metal atoms with the PS-ODN. The ultraviolet absorbance of the resuspended material was determined at a wavelength of 270 nanometers, the peak of absorbance for PS-ODNs, using a Gilford spectrophotometer, Model 240 (Gilford Instrument Laboratories, Oberlin, Ohio). TABLE 1 shows the ratio of moles of metal to moles of sulfur in the PS-ODN, and its corresponding correlation coefficient. A lower ratio demonstrates a higher binding affinity between the target metal ion and the PS-ODN.

As shown in TABLE 1, the rank order of metal affinity was: Hg, Fe, Sn, Pb, Cd≦≦Cu, Cr, Sr, U≦Zn, Co, Cs≦Ca, Mg≦Ni. These data show that the most toxic heavy metal ions (Hg, Pb, Cd) are among the most avidly bound to the PS-ODN, whereas the essential nutrient elements Zn, Ca and Mg bind with much less affinity. This unexpected result is extremely important because it indicates that use of PS-ODN in doses sufficient to remove heavy metals should not deplete trace mineral elements essential to maintenance of normal physiologic homeostasis.

TABLE 1

| Metal binding capcacity of PS-ODNs | | |
|---|---|---|
| Metal | Oligonucleotide Binding[a] | Correlation Coefficient[b] |
| Cadmium (CdCl$_2$) | 7.1 | 0.999 |
| Calcium (CaCl$_2$) | 124.5 | 0.957 |
| Cesium (CsCl) | 77.0 | 0.942 |
| Chromium (Cr$_3$(SO$_4$)$_3$) | 23.2 | 0.963 |
| Cobalt (CoCl) | 69.1 | 0.260 |
| Copper (CuSO$_4$) | 14.7 | 0.842 |
| Iron (FrCl$_3$) | 3.2 | 0.949 |

TABLE 1-continued

| Metal binding capcacity of PS-ODNs | | |
|---|---|---|
| Metal | Oligonucleotide Binding[a] | Correlation Coefficient[b] |
| Lead (Pb(NO$_2$)$_2$) | 6.5 | 0.883 |
| Magnesium (MgCl$_2$) | 189.4 | 0.395 |
| Mercury (HgCl$_2$) | 3.0 | 0.894 |
| Nickel (NiCl$_2$) | 1012.0 | 0.763 |
| Strontium (SrCl$_2$) | 27.9 | 0.460 |
| Tin (SnCl$_2$) | 6.0 | 0.948 |
| Uranium (UO$_2$(C$_2$H$_3$O$_2$)) | 29.5 | 0.996 |
| Zinc (ZnCl) | 44.4 | 0.605 |

[a]Ratio of moles metal to moles sulfur in PS-ODN
[b]Data fit to sigmoidal curve

EXAMPLE 5

Demonstration of the Site in a PS-ODN to Which Metal Ions Bind

An unusual oligomeric phosphorothioate structure, a 26-mer identified as "C-E-C-P(S)", was synthesized by the procedures described in EXAMPLE 1. The unusual nature of this oligomeric molecule is its abasic nature; i.e., it is essentially a phosphorothioate backbone comprising 26 deoxyribose linkages containing no nucleotide bases except for a deoxycytidine nucleotide base at each terminal position of the molecule. Hence, the name "C-E-C-P(S)" derives essentially from the "deoxycytidine-empty-deoxycytidine" base arrangement.

When mixed with mercuric chloride (HgCl$_2$), using methods described in EXAMPLE 4, this unusual oligomeric phosphorothioate developed a single, strong adsorption peak at 240 nanometers which was not seen in the absence of the metal salt. This single absorption peak was also seen when C-E-C-P(S) molecules were mixed with a zinc salt (ZnCl), but the intensity of the peak was diminished in comparison with the peak generated using the mercury salt. Because a chelate between the phosphorothioate backbone and the metal ion could only form between the sulfur atoms in the phosphorothioate structure, the data indicate that the metal ion is bound between adjacent charged P-S sites, as follows:

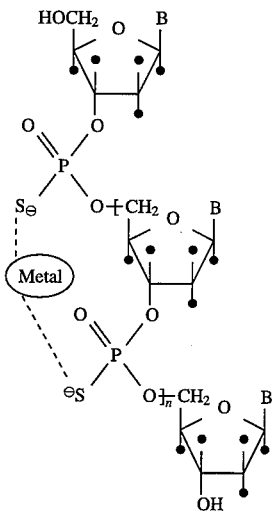

In practicing the present invention, a number of heavy-metal binding agents can be utilized to bind or to chelate heavy metal atoms in the tissues of a host organism, provided that such binding or chelating generates a complex which is excreted from the host organism and is not readily sequestered in the tissues of the host organism. While the binding agents herein described are described in conjunction with preferred embodiments and specific examples, the listing of these selected binding agents is not meant to imply that they are the only ones which may be utilized in practicing this invention. One of ordinary skill in the art, with the aid of the present disclosure, can effect various changes, substitutions of equivalents and other alterations to the methods and compositions herein set forth, in order to practice this invention. Therefore, the protection granted by Letters Patent should not be limited except by the language of the claims as set forth below.

What is claimed is:

1. A method of treating an animal suffering from heavy metal poisoning comprising:

a) chelating heavy metal ions in said animal by administering a phosphorothioate oligonucleotide to said animal in an amount sufficient to chelate heavy metals and to cause excretion thereof; and b) monitoring the presence of chelated metals in the urine of said animal.

2. A method for removing toxic heavy metal ions from an animal suffering from heavy metal toxicity comprising:

a) chelating heavy metal ions in said animal by administering to said animal a phosphorothioate oligonucleotide in an amount sufficient to chelate and cause excretion of said metal ions wherein said phosphorothioate oligonucleotide has the following formula:

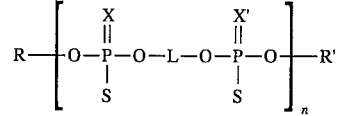

wherein L is a linking group consisting of a deoxyribonucleotide moiety; X and X' can be the same or different and are oxygen or sulfur; R and R' are terminal moieties which can be the same or different and are deoxyribonucleotide moieties and; n is a number between 2 and about 30, a and b) monitoring the presence of chelated metals in urine excreted from said animal.

3. The method of claim 1 or claim 2, wherein said animal is a human.

4. A method according to claim 1 or claim 2 wherein the nucleotide sequence of said phosphorothioate oligonucleotide is SEQ ID NO:1.

5. The method of claim 1 or claim 2, wherein said animal is a rat.

* * * * *